United States Patent
Yang et al.

(10) Patent No.: US 6,656,156 B2
(45) Date of Patent: Dec. 2, 2003

(54) DUAL SURFACE PROTECTION COATING FOR DRUG DELIVERY BALLOON CATHETERS AND STENTS

(75) Inventors: Dachuan Yang, Plymouth, MN (US); Joel Stanslaski, New Hope, MN (US); Lixiao Wang, Maple Grove, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/154,186

(22) Filed: May 22, 2002

(65) Prior Publication Data

US 2002/0151844 A1 Oct. 17, 2002

Related U.S. Application Data

(62) Division of application No. 09/243,580, filed on Feb. 3, 1999, now Pat. No. 6,419,692.

(51) Int. Cl.[7] .............. A61M 29/00; A61M 31/00; A61M 37/00
(52) U.S. Cl. ............ 604/103.02; 604/103.06; 604/103.12
(58) Field of Search ............ 604/103.02, 96.01, 604/103.05, 103.06, 103.08, 103.11, 103.12, 103.13, 103.14, 915, 890.1; 606/192, 194

(56) References Cited

U.S. PATENT DOCUMENTS

| 4,391,797 A | 7/1983 | Folkman et al. |
|---|---|---|
| 4,459,317 A | 7/1984 | Lambert |
| 4,487,808 A | 12/1984 | Lambert |
| 4,768,507 A | 9/1988 | Fischell et al. |
| 4,770,664 A | 9/1988 | Gogolewski |
| 4,923,464 A | 5/1990 | DiPisa, Jr. |
| 4,969,890 A | 11/1990 | Sugita et al. |
| 4,994,071 A | 2/1991 | MacGregor |
| 5,019,096 A | 5/1991 | Fox, Jr. et al. |
| 5,092,885 A | 3/1992 | Yamada et al. |

(List continued on next page.)

FOREIGN PATENT DOCUMENTS

| EP | 0 274 846 B1 | 7/1988 |
|---|---|---|
| EP | 0 294 905 A1 | 12/1988 |
| EP | 0 470 246 B1 | 2/1992 |
| EP | 0 470 569 A1 | 2/1992 |
| EP | 0 543 653 A1 | 5/1993 |

(List continued on next page.)

OTHER PUBLICATIONS

Bartoli et al., 1990, "In Vitro and In Viro Antitumoral Activity of Free and Encapsulated Taxol," *J. Microencapsulation*, 7(2):191–97.

(List continued on next page.)

*Primary Examiner*—Brian L. Casler
*Assistant Examiner*—Mark K Han
(74) *Attorney, Agent, or Firm*—Pennie & Edmonds LLP

(57) ABSTRACT

The invention relates to a medical device, such as a stent or a balloon catheter that includes an expandable body portion which has an exterior surface that contacts a vessel wall during treatment. The medical device includes a first coating disposed over at least a portion of the exterior surface. The first coating includes a therapeutic substance that is intended for controlled release from the exterior surface. The medical device further includes a second coating overlaying at least a substantial portion of the first coating. The second coating includes a material that is generally impervious to elution of the therapeutic substance therethrough when the body portion is inserted into the vessel lumen. The material of the second coating is relatively inelastic so that the second coating fractures during expansion of the body portion to allow elution of the therapeutic substance through fissures formed in the second coating.

5 Claims, 2 Drawing Sheets

U.S. PATENT DOCUMENTS

| | | |
|---|---|---|
| 5,102,402 A | 4/1992 | Dror et al. |
| 5,102,417 A | 4/1992 | Palmaz |
| 5,222,971 A | 6/1993 | Willard et al. |
| 5,282,823 A | 2/1994 | Schwartz et al. |
| 5,304,121 A | 4/1994 | Sahatjian |
| 5,324,261 A | 6/1994 | Amundson et al. |
| 5,370,614 A | 12/1994 | Amundson et al. |
| 5,380,299 A | 1/1995 | Fearnot et al. |
| 5,383,928 A | 1/1995 | Scott et al. |
| 5,419,760 A | 5/1995 | Narciso, Jr. |
| 5,423,885 A | 6/1995 | Williams |
| 5,443,458 A | 8/1995 | Eury |
| 5,443,496 A | 8/1995 | Schwartz et al. |
| 5,447,724 A | 9/1995 | Helmus et al. |
| 5,449,372 A | 9/1995 | Schmaltz et al. |
| 5,449,382 A | 9/1995 | Dayton |
| 5,464,650 A | 11/1995 | Berg et al. |
| 5,512,055 A | 4/1996 | Domb et al. |
| 5,514,154 A | 5/1996 | Lau et al. |
| 5,527,337 A | 6/1996 | Stack et al. |
| 5,545,208 A | 8/1996 | Wolff et al. |
| 5,562,922 A | 10/1996 | Lambert |
| 5,569,463 A | 10/1996 | Helmus et al. |
| 5,578,075 A | 11/1996 | Dayton |
| 5,591,227 A | 1/1997 | Dinh et al. |
| 5,605,696 A | 2/1997 | Eury et al. |
| 5,609,629 A | 3/1997 | Fearnot et al. |
| 5,616,608 A | 4/1997 | Kinsella et al. |
| 5,624,411 A | 4/1997 | Tuch |
| 5,626,862 A | 5/1997 | Brem et al. |
| 5,637,113 A | 6/1997 | Tartaglia et al. |
| 5,651,986 A | 7/1997 | Brem et al. |
| 5,674,241 A | 10/1997 | Bley et al. |
| 5,674,242 A | 10/1997 | Phan et al. |
| 5,679,400 A | 10/1997 | Tuch |
| 5,697,967 A | 12/1997 | Dinh et al. |
| 5,700,286 A | 12/1997 | Tartaglia et al. |
| 5,709,874 A | 1/1998 | Hanson et al. |
| 5,716,981 A | 2/1998 | Hunter et al. |
| 5,733,925 A | 3/1998 | Kunz et al. |
| 5,735,897 A | 4/1998 | Buirge |
| 5,755,769 A | 5/1998 | Richard et al. |
| 5,776,184 A | 7/1998 | Tuch |
| 5,779,732 A | 7/1998 | Amundson |
| 5,824,048 A | 10/1998 | Tuch |
| 5,824,059 A | 10/1998 | Wijay |
| 5,837,008 A | 11/1998 | Berg et al. |
| 5,868,781 A | 2/1999 | Killion |
| 6,048,620 A | 4/2000 | Zhong |
| 6,099,561 A | 8/2000 | Alt |
| 6,099,563 A | 8/2000 | Zhong |
| 6,120,847 A | 9/2000 | Yang et al. |
| 6,129,755 A | 10/2000 | Mathis et al. |
| 6,280,411 B1 * | 8/2001 | Lennox ................. 604/103.05 |

FOREIGN PATENT DOCUMENTS

| | | |
|---|---|---|
| EP | 0 551 183 A1 | 7/1993 |
| EP | 0 567 816 A1 | 11/1993 |
| EP | 0 568 310 A1 | 11/1993 |
| EP | 0 604 022 A1 | 6/1994 |
| EP | 0 623 354 A1 | 11/1994 |
| EP | 0 706 376 A1 | 4/1996 |
| WO | WO 90/01969 | 3/1990 |
| WO | WO 90/13332 | 11/1990 |
| WO | WO 91/07154 | 5/1991 |
| WO | WO 91/10424 | 7/1991 |
| WO | WO 91/11193 | 8/1991 |
| WO | WO 91/12779 | 9/1991 |
| WO | WO 92/00747 | 1/1992 |
| WO | WO 92/12717 | 8/1992 |
| WO | WO 92/15286 | 9/1992 |
| WO | WO 93/06792 | 4/1993 |
| WO | WO 93/11120 | 6/1993 |
| WO | WO 94/21308 | 9/1994 |
| WO | WO 96/02091 A1 | 2/1996 |
| WO | WO 96/03984 | 2/1996 |
| WO | WO 96/25176 | 8/1996 |
| WO | WO 96/26689 | 9/1996 |
| WO | WO 98/23228 | 6/1998 |
| WO | WO 98/36784 | 8/1998 |

OTHER PUBLICATIONS

Cox et al., 1992, "Effect of Local Delivery of Heparin and Methotrexate on Neointimal Proliferation in Stented Porcine Coronary Arteries," *Coronary Artery Disease*, 3(3):237–248.

Cox et al., 1991, "Local Delivery of Heparin and Methotrexate Fails to Inhibit In Vivo Smooth Muscle Cell Proliferation," *Supplement to Circulation Abstracts from the 64th Scientific Sessions*, 84(4):II–71, Abstract No. 0284.

Dev et al., 1993, "Kinetics of Drug Delivery to the Arterial Wall Via Polyurethane Coated Removable Nitinol Stent–Comparative Study of 2 Drugs," *Circulation Abstracts from the 66th Scientific Sessions*, 88(4):I–3, Abstract No. 1657.

Jampel et al., 1991, "In Vivo Release of Hydrophobic Drugs from Polyanhydride Disks," *Ophthalmic Surgery*.

Lambert et al., 1993, "A New Method For Arterial Drug Delivery Via Removable Stent," *JACC*, 21(2):483A, Abstract No. 834–2.

Lambert et al., 1993, "Localized Arterial Drug Delivery From A Polymer Coated Removable Metallic Stent: Kinetics and Bioactivity of Forskolin," *Circulation Abstracts from the 66th Scientific Sessions*, 88(4, Part 2):I–3, Abstract No. 1659.

Moses et al., dated prior to Jan. 8, 1999, *Inhibitors of Antiogenesis*, Review, The Children's Hospital Medical Center, Boston, MA.

Pitt et al., 1980, "The Design of Controlled Drug Delivery Systems Based on Biodegradable Polymers," *Progress in Contraceptive Delivery Systems*, MTP Press, Lancaster, pp. 17–18.

Tang et al., 1993, "Regression of Collagen–Induced Arthritis with Taxol, a Microtubule Stabilizer," *Arthritis Rheum.*, 36(9)(Suppl.):42.

"A Powerful Case For LOPID," Parke–Davis, dated prior to Jan. 8, 1999.

Whitborne, Presentation at the 2nd International Coronary Stenting Summit (Mar. 1–2, 1991).

* cited by examiner

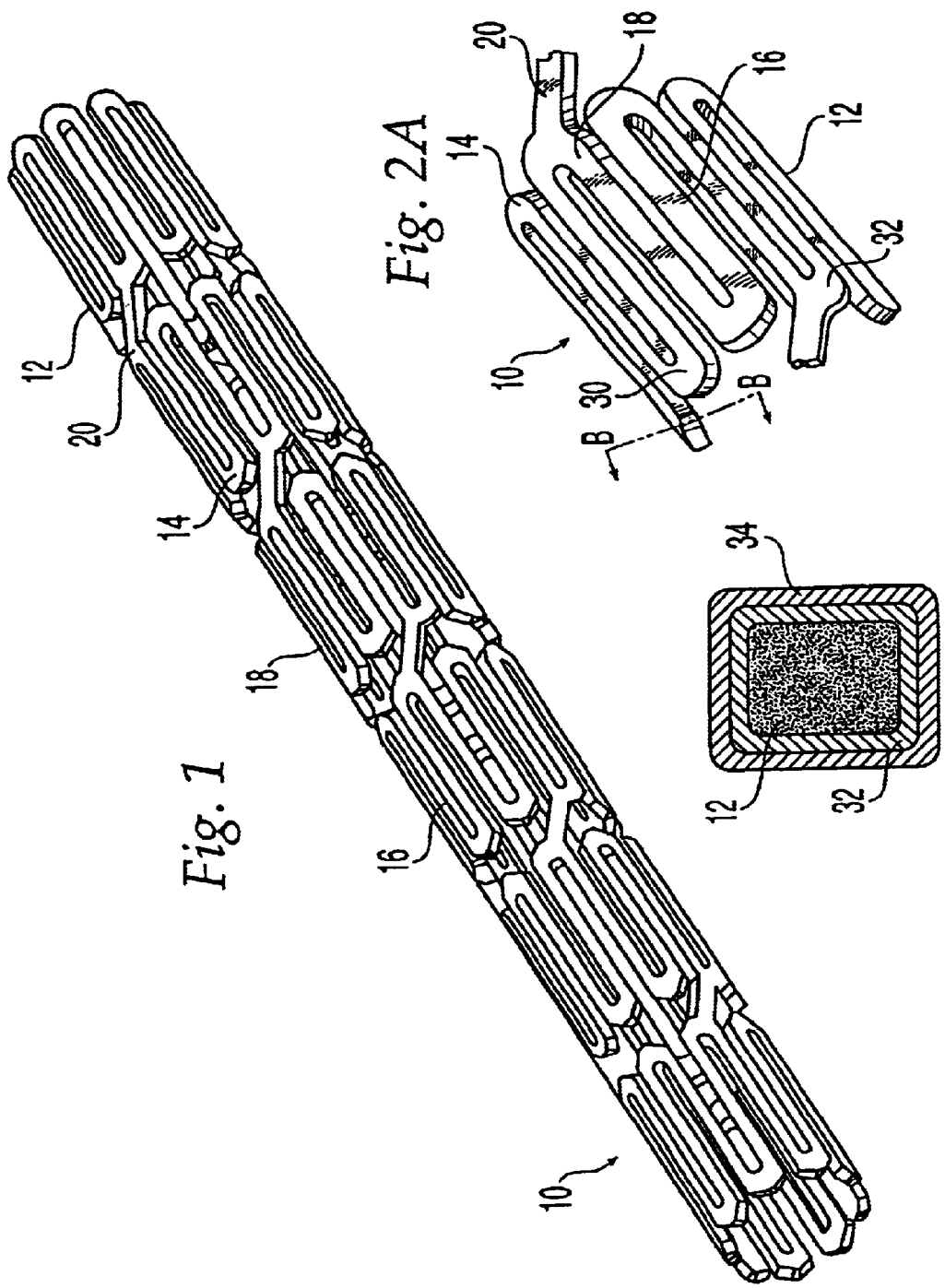

DUAL SURFACE PROTECTION COATING FOR DRUG DELIVERY BALLOON CATHETERS AND STENTS

This is a division of application Ser. No. 09/243,580, filed Feb. 3, 1999, now U.S. Pat. No. 6,419,692.

FIELD OF THE INVENTION

The present invention pertains to medical apparatus, particularly expandable stents, having a surface coating applied over a portion of the apparatus' surface. In particular, the present invention relates to a generally impermeable surface coating which protects therapeutic materials disposed under the surface coating from the surrounding environment until the release of these materials is desired and achieved through fracture of the surface coating.

BACKGROUND OF THE INVENTION

While angioplasty has gained wide acceptance, abrupt closure and restenosis have been identified as possible subsequent occurrences. Abrupt closure refers to the acute occlusion of a vessel immediately after or within the initial hours following a dilation procedure. Abrupt closure can result in myocardial infarction if blood flow is not restored in a timely manner. The primary mechanisms of abrupt closures are arterial dissection and/or thrombosis. Restenosis refers to the re-narrowing of an artery after an initial successful angioplasty. Restenosis occurs primarily within the initial six months after angioplasty, and is believed due to the proliferation and migration of the cellular components of the arterial wall.

Endovascular stents are placed in the dilated segment of a vessel lumen to mechanically block the effects of abrupt closure and restenosis. In U.S. Pat. No. 5,514,154, Lau et al. disclose an expandable stent which is relatively flexible along its longitudinal axis. This flexibility facilitates delivery of the stent through tortuous body lumens. Additionally, the stent is stiff and stable enough radially, in an expanded condition, to maintain the patency of a body lumen such as an artery when implanted therein. Such stents have not, however, eliminated abrupt closure and have not eliminated restenosis.

Recent developments have led to stents which attempt to provide antithrombogenic and other medications to regions of a blood vessel which have been treated by angioplasty or other interventional techniques. In U.S. Pat. No. 5,464,650, Berg et al. disclose a method for making an intravascular stent by applying to the stent, and in particular to its tissue-contacting surface, a solution which includes a solvent, a polymer dissolved in the solvent, and a therapeutic substance dispersed in the solvent. After the solution is applied to the stent, the solvent is then evaporated leaving the polymer/therapeutic agent surface treatment. Berg et al. assert that these devices are capable of providing both short term medication delivery, over the initial hours and days after the treatment, as well as long term medication delivery, over the weeks and months after the treatment.

An ongoing problem with present drug release coatings applied to devices such as stents is achieving a therapeutic concentration of a drug locally at a target site within the body without producing unwanted systemic side effects. Implantation of vascular stents is a prime example of a situation where local therapy is needed with drugs that also produce unwanted systemic side effects. Because the stent is placed within a flowing blood stream, during placement and upon implantation, potential unwanted systemic effects may result from undesirable quantities of the therapeutic substance entering the blood stream. Further, if quantities of therapeutic substance are released into the blood stream during positioning of the stent, less is available for actual local treatment when the stent is expanded, resulting in potential inadequate local dosing. The many attempts to effectuate local drug delivery via endovascular means have failed to address controlling of release of the therapeutic substance systemically during implantation and following implantation.

Therefore, there exists a need in the art for a means and a method for providing local therapy which can sustain high local concentrations of therapeutic drugs at a predetermined site without producing unwanted side effects, such as unwanted quantities of the drugs entering the blood stream. There especially exists a need to provide adequate concentration of therapeutic agents directly to the boundary layer of blood flow near the vessel wall at a targeted treatment area which greatly reduces the systemic side effects and amount of drug needed to achieve a therapeutic result.

SUMMARY OF THE INVENTION

The present invention provides a medical device, and a method for manufacturing the medical device, which includes a thin layer overlying a releasable drug or therapeutic substance layer. The thin overlying layer protects the drug layer during positioning and deployment of the medical device within a body lumen. The thin overlying layer is selected to be of a polymeric material and selected thickness which essentially prevents elution of the therapeutic substance until the medical device is placed at a desired location within the body lumen and expanded. The expansion of the medical device produces fissures throughout the overlying layer through which the therapeutic substance elutes. With this design, the therapeutic substance is assured to be applied at the local selected delivery site with substantially reduced systemic effect from the drug entering the blood stream and traveling away from the deployment site.

The present invention is useful in conjunction with local delivery of drugs or therapeutic substances on an expandable stent within the vascular system. The invention may also be utilized in conjunction with drug delivery from balloon catheters or stents for use in other body lumens. The invention is particularly useful when utilizing a water soluble drug or therapeutic substance which tends to dissolve and migrate within a blood or other body fluid environment. It is also beneficial to use the overlying protective coating when the drug is placed on the medical device with a hydrophilic polymeric carrier, which is intended to dissolve and release the drug or therapeutic substance over an extended period of time when the device is placed within the body lumen at a selected site. The second or overlying layer of protective material, which fractures upon expansion of the medical device, is preferably a biodegradable polymer which is absorbed by the body over an extended period of time, but which prevents elution of the drug or therapeutic substance during the time required to place the device within the vessel lumen.

In preferred embodiments of the present invention, the medical device is one which is designed for treating a vessel lumen wall, such as an arterial wall, in conjunction with treating a stenosis at the same location. The medical device preferably includes a body portion having an exterior surface defined thereon with the body portion being expandable from a first position, wherein the body portion is sized for insertion into the vessel lumen, to a second position, wherein at least a portion of the exterior surface of the medical device is in contact with the lumen wall. A preferred medical device includes a first coating disposed over at least a portion of the exterior surface of the body portion of the medical device with the first coating including, at least in part, a drug or therapeutic substance for treating the vessel wall. In preferred embodiments, the first coating includes the drug or therapeutic substance in combination with a polymeric carrier which preferably controls the rate of release of the drug or therapeutic substance over an extended period of time. The therapeutic substance or drug releases from the first coating, in preferred embodiments, in response to contact with fluid within the vessel lumen or at the vessel wall.

Preferred drugs or therapeutic substances which may be incorporated into the first coating or included in the first coating with a polymeric carrier include heparin, antibiotics, radiopaque agents, anti-thrombogenic agents, anti-proliferative agents, antiangiogenic agents, and combinations thereof. Specific drugs can include taxol, taxol derivatives, colchicine, vinblastine or epothilones, which are classified as anti-proliferative and anti-angiogenic agents. A preferred polymeric carrier for the drug or therapeutic substance is a biodegradable agent which can include polylactic acid, polyglycolic acid, polyethylene oxide, polycaprolactones, polydioxanone, poly(orthoesters), polyanhydrides, polyphosphazenes, and mixtures or copolymers of these polymeric materials. The polymeric material could also be selected to include non-biodegradable polymers such as polyurethane, polysiloxane, polyacrylate and mixtures and copolymers of these polymeric materials.

The present invention includes a second coating preferably overlying at least a substantial portion of the first coating. The second coating includes at least in part a material that is generally impervious to elution of the drug or therapeutic substance therethrough when the body portion of the medical device is in the first position, while being inserted and placed within the lumen. Further, the material of the second coating is preferably relatively inelastic so that the second coating fractures during expansion of the body portion of the medical device to the second position to allow elution of the drug or therapeutic substance through fissures formed through the surface of the second coating. The second coating of the present invention works particularly well in combination with expandable stents or drug delivery balloons. The second coating is preferably a polymeric material which can include polylactic acid, polyglycolic acid, polyanhydrides, polyphosphazenes, poly(orthoesters) and mixtures and copolymers of these polymeric materials. In preferred embodiments, the thickness of the second coating is about 0.01 $\mu$m to about 5 $\mu$m.

A preferred medical device of the present invention includes a stent which is a generally tubular structure having an exterior surface defined by a plurality of interconnected struts having interstitial spaces therebetween. The generally tubular structure is expandable from a first position, wherein the stent is sized for intravascular insertion, to a second position, wherein at least a portion of the exterior surface of the stent contacts the vessel wall. The expanding of the stent is accommodated by flexing and bending of the interconnected struts throughout the generally tubular structure. The second coating overlying the stent surface which protects the therapeutic substance or drug during placement, fractures upon flexing and bending of the struts on the stent during expansion.

The second coating of the present invention can also be utilized on a medical device, such as a balloon catheter, wherein the second coating is included on at least a portion of the balloon which is expandable from a folded or unexpanded first position to an expanded second position which is adapted for treatment of the vascular lumen wall by contact with at least a portion of the exterior surface of the balloon. The second coating overlying the drug or therapeutic substance is again relatively inelastic so that upon expansion of the balloon, the coating fractures to allow elution of the drug or therapeutic substance through fissures formed in the coating.

Additional features of the invention and the advantages derived therefrom, and the various scopes and aspects of the invention will become apparent from the drawings, the description of the preferred embodiments of the invention, and the claims.

DESCRIPTION OF THE DRAWINGS

FIG. 1 is a perspective view of a stent in accordance with an exemplary embodiment of the present invention;

FIG. 2A is a magnified, partial perspective view of FIG. 1 in a first, non-expanded form;

FIG. 2B is a magnified, cross-sectional view of FIG. 2A across line B—B illustrating the polymeric surface coating selectively applied to wire members;

DETAILED DESCRIPTION OF THE DRAWINGS

Figure 3:
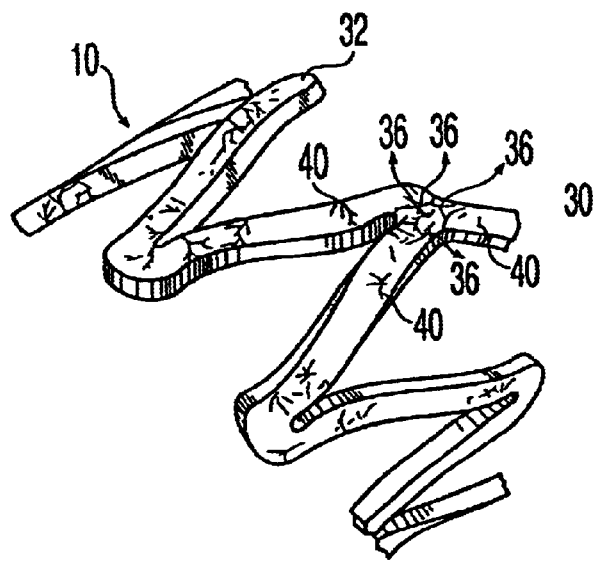
FIG. 3 is a magnified, partial perspective of FIG. 2A in a second, expanded form, illustrating the polymeric fragmentation and subsequent elution of a therapeutic substance arising from the expansion of the stent.

Stents of the type shown in FIG. 1, disclosed in U.S. patent application Ser. No. 08/874,190, filed Jun. 13, 1997, entitled "Polymeric Layered Stents", perform the desired applications of dilating and maintaining the patency of various lumen passages within the human body. The above application is assigned to the assignee of the present invention, and the disclosure is hereby incorporated by reference.

Referring now to the drawings wherein like reference numerals refer to like elements throughout the several views, FIG. 1 shows a perspective view of a stent 10, in a non-expanded form, in accordance with the present invention. The skeletal frame of the stent 10 preferably includes wire-like members 12 forming a distinct, repetitive serpentine pattern. This repetitive serpentine pattern consists of multiple U-shaped curves 14. These U-shaped curves 14 form interstitial spaces 16. With no recognizable beginning or end to this serpentine pattern, wire 12 forms expandable serpentine element 18. Serpentine elements 18 are arranged along the longitudinal axis of the stent 10 so that the U-shaped curves 14 of abutting serpentine elements 18 may be joined through an interconnecting element 20. Through the interconnecting elements 20, a continuous wire 12 framework is created between multiple serpentine elements 18 forming the stent 10.

A surface treatment 30 is selectively applied to the skeletal frame of the stent 10. This surface treatment 30 comprises at least two overlying coatings selectively applied to at least a portion of the exterior surface of the wire-like members 12. The function of the two overlying coatings is best understood from the depictions in FIG. 2A, FIG. 2B, and FIG. 3, as described below.

Referring now to FIG. 2A and FIG. 2B, a portion of the stent of FIG. 1 is depicted in magnified view with the first coating 32 disposed over at least a portion of the exterior surface of wire-like members 12. The first coating 32 includes at least in part, a therapeutic substance or drug. In a preferred embodiment, the therapeutic substance is comprised, at least in part, of an anti-proliferative or anti-angiogenic drug. This therapeutic substance is typically dispersed and contained in a polymeric carrier matrix forming the first coating 32. The use of a matrix allows for a selectively controlled elution rate for the incorporated drug or therapeutic substance. By modifying the ratio of polymeric carrier to therapeutic substance, the ability of the therapeutic substance to elute from the carrier either increases or decreases. In a further preferred embodiment, the elution rate of the therapeutic substance may be controlled by utilizing a biodegradable polymeric camer. Polylactic acid (PLA), polyglycolic acid, polyethylene oxide (PEO), polycaptrolactone are examples of such polymeric carriers. Either the homopolymer or the copolymer forms of these materials may be utilized in the incorporation with the therapeutic substance. Other polymeric carriers which may be utilized include: polyurethane, polysiloxane, polyacrylate and their mixtures or copolymers.

Other therapeutic substances or drugs can also be incorporated into the first coating, either alone or in combination with the anti-proliferative or anti-angiogenic agents. These drugs can include heparin, antibiotics, radiopaque agents and anti-thrombogenic agents.

These components may be added to the anti-proliferative or anti-angiogenic drug in order to alter the function of the therapeutic substance. In a preferred embodiment, to prevent the aggregation of platelets, fibrin, clotting factors, and cellular elements of the blood as a result of the implementation of the stent 10, the anti-proliferative drug or antiangiogenic drug may also contain an additional anti-thrombogenic drug that may be incorporated with the other drugs forming the first coating 32. In a further preferred embodiment, the anti-angiogenic drug is Taxol, Taxol derivatives, colchicine, vinblastine, or epothilone.

The second coating 34, preferably the outermost coating, overlays at least a substantial portion of the first, or previous coating 32. This second coating 34 comprises a material that is generally impervious to the elution of the therapeutic substance or drug incorporated in the first coating 32. The second coating 34 acts as a protective coating for the drug or therapeutic substance which prevents the drug or therapeutic substance from elution prior to proper placement within the vessel lumen at a treatment site. Further, this protective layer prevents physical damage to the drug coating layer during insertion. In preferred embodiments, release of the therapeutic substance is enhanced by contact with water or other liquids present in the blood or other body lumen. This is particularly true in embodiments which incorporate a drug or therapeutic substance which is water soluble or a polymeric carrier that is hydrophilic and tends to release more therapeutic substance upon contact with a liquid such as water. Thus, the second coating 34 or overlayer of protective coating is preferably impervious to water or body fluids, at least for the time period required for placement of the stent within the vessel lumen at the treatment site. In this way, the elution of the drug is prevented until the medical device or stent is located at the required treatment site.

Thus, in use, the stent or other medical device of the present invention is coated with first a drug or therapeutic substance, followed by an overlying coat of a second coating or protective coating. The first coating may be placed on the medical device while in an unexpanded configuration, or alternatively, the device may be expanded for coating and then contracted for placement in the vessel. The second coating, or protective coating, is made to overly the first coating while the medical device is in the first position for insertion in the lumen. In preferred embodiments, the second coating material is relatively inelastic so that the second coating fractures during expansion of the body portion of the medical device to the second position. The portion of the stent depicted in FIG. 2A is depicted in FIG. 3 in an expanded state, which clearly indicates a multiplicity of fractures or fissures 40 throughout the second coating 34 with the drug or therapeutic substance 36 eluting through the fissures 40.

As previously stated, the second coating is preferably a polymeric coating which is relatively inelastic so that the expansion of the stent or other medical device causes fractures to form within the coating surface. These fractures allow the elution of the drug or therapeutic substance therethrough. A preferred polymeric material includes polylactic acid, polyglycolic acid, polyanhydrides, polyphosphazene or poly(orthoester). The thickness of the second coating is preferably about 0.01 $\mu$m to about 5.0 $\mu$m. The second coating is preferably biodegradable or bioabsorbable so that over time the second coating is absorbed by the body.

The present invention has been discussed in conjunction with a preferred stent. However, it is recognized that the invention disclosed herein may be utilized with any stent design which is expanded from a first position to a second position with resultant fracture of a second protective coating thereon. Preferred stents include those generally tubular structures having an exterior surface defined by a plurality of interconnected struts having interstitial spaces therebetween. In the first position, the stent is sized so that it may be inserted into the lumen of the intravascular system. Once located at a point of treatment, the stent may be expanded to a second position wherein at least a portion of the exterior surface contacts the wall of the vessel lumen.

Figure 4:
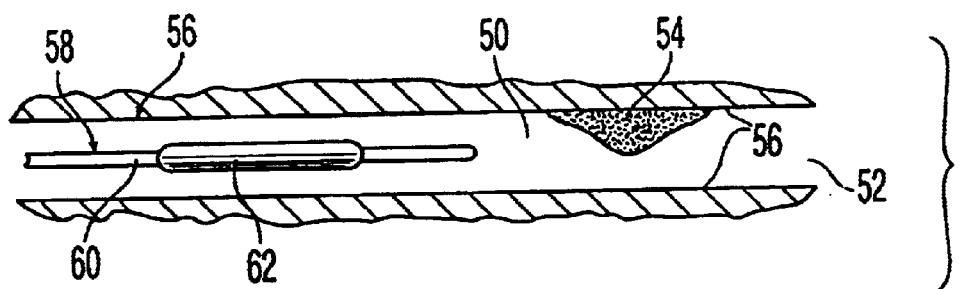
FIG. 4 is a schematic representation of a catheter of the present invention having a folded balloon in a first position thereon inserted within a vessel lumen.
Figure 5:
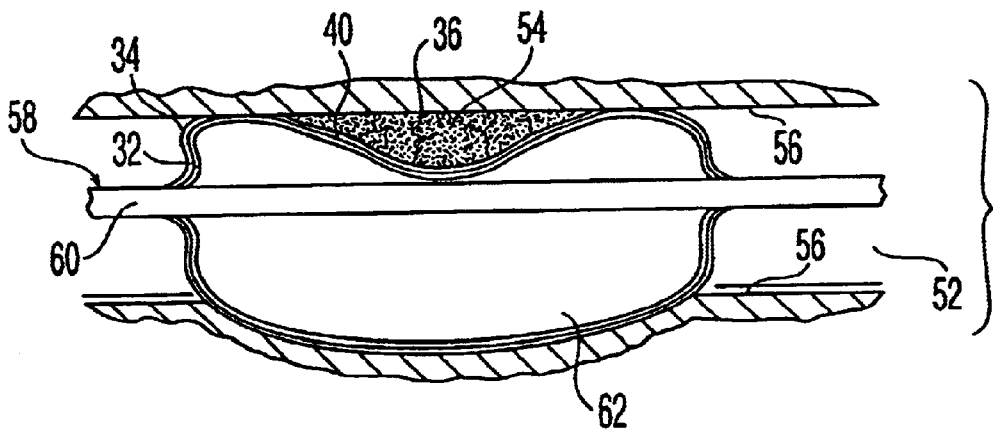
FIG. 5 is a schematic representation of the catheter of FIG. 4 having the balloon in a second expanded position for treatment of the vessel wall.

The use of a second protective coating, as described above for a stent, can also be incorporated into a medical device such as a balloon-type drug delivery catheter or balloon dilatation catheter. FIGS. 4 and 5 depict the incorporation of the present invention into a balloon catheter design. The materials and therapeutic substances discussed above are equally applicable in the present balloon catheter embodiment.

Now referring to FIG. 4, a vessel 50 within the vascular system is depicted schematically with a lumen 52 defined therethrough which is partially occluded by a stenosis 54 therein. The lumen is defined by lumen walls 56 as indicated. A balloon catheter 58 is depicted as being inserted into the vessel lumen 52. The balloon catheter 58 includes a shaft 60 having disposed on a distal portion thereof an inflatable balloon 62. The balloon 62 is depicted in a folded or uninflated profile which is suitable for inserting into the lumen 52 of the blood vessel 50.

The balloon 62 includes a drug or therapeutic substance coated on the surface thereof. In preferred embodiments, the entire surface of the balloon is coated with a drug or therapeutic substance, either alone or in a polymeric carrier, while the balloon is in an inflated position so that the entire surface thereof includes the drug or therapeutic substance thereon. The second coating or protective coating is applied while the balloon is in a deflated or low profile condition.

Again, this protective coating prevents the elution of the drug from the surface of the balloon which is exposed during insertion of the catheter prior to inflation of the balloon at the treatment site.

Referring now to FIG. 5, the balloon catheter 58 of FIG. 4 is depicted with the balloon 62 located across the stenotic area 54 in an inflated condition. As shown in FIG. 5, the balloon 62 includes a first coating 32, which includes the drug or therapeutic substance, and a second coating 34, which is the protective coating which was applied when the balloon 62 was in deflated condition. FIG. 5 schematically depicts the multiplicity of fissures 40 which are formed in the balloon surface second coating 34 upon expansion of the balloon 62. This results in elution of the drug or therapeutic substance 36 through such fissures 40 into the treatment area.

Numerous characteristics and advantages of the invention covered by this document have been set forth in the foregoing description. It will be understood, however, that this disclosure is, in many aspects, only illustrative. Changes may be made in details, particularly in matters of shape, size, and arrangement of parts without exceeding the scope of the invention. The invention scope is defined, of course, in the language within the appended claims are expressed.

What is claimed is:

1. A catheter for drug delivery comprising:
    a longitudinally extending shaft having a distal end and a proximal end, the shaft defining an inflation lumen;
    a balloon member having an exterior surface disposed proximate the distal end of said shaft in fluid communication with said inflation lumen, said balloon member expandable from a first position, wherein said balloon member is sized for intravascular insertion, to a second position, wherein at least a portion of said exterior surface contacts a vessel wall;
    a first coating disposed over at least a portion of said exterior surface of said balloon member, said first coating comprising a therapeutic substance; and
    a second coating overlying at least a substantial portion of said first coating when said balloon member is in said first position, wherein said second coating comprises a relatively inelastic material so that said second coating fractures in response to expansion of said balloon member to said second position to allow elution of said therapeutic substance through fissures formed in said second coating.

2. The catheter of claim 1, wherein said therapeutic substance would elute from said exterior surface in response to fluid contact if said second coating were absent.

3. The catheter of claim 1, wherein said material of said second coating comprises a polymeric material selected from the group consisting of polylactic acid, polyglycolic acid, polyanhydrides, polyphosphazenes, poly(orthoesters) and mixtures and copolymers thereof.

4. The catheter of claim 1, wherein said therapeutic substance is selected from the group consisting of: taxol, taxol derivatives, colchicine, vinblastine and epothilone.

5. The catheter of claim 1, wherein said therapeutic substance is elutable when contacted with water-containing fluids if said second coating were absent.

* * * * *